United States Patent [19]
Inoue

[11] Patent Number: 5,195,972
[45] Date of Patent: Mar. 23, 1993

[54] BALLOON CATHETER ASSEMBLY

[76] Inventor: Kanji Inoue, 13, Shimogamo-Miyazaki-cho 98 banchi, Sakyo-ku, Kyoto-fu, Japan

[21] Appl. No.: 731,150

[22] Filed: Jul. 15, 1991

Related U.S. Application Data

[63] Continuation of Ser. No. 427,345, Oct. 27, 1989.

[30] Foreign Application Priority Data

Oct. 28, 1988 [JP] Japan ............... 63-272366
Oct. 28, 1988 [JP] Japan ............... 63-272367

[51] Int. Cl.⁵ ............................................ A61M 29/00
[52] U.S. Cl. ................................................... 604/103
[58] Field of Search ............................. 604/96–103, 604/283; 128/207.14–207.15; 606/192–194

[56] References Cited

U.S. PATENT DOCUMENTS

| | | | |
|---|---|---|---|
| 2,930,377 | 3/1960 | Cowley | 604/103 |
| 4,327,736 | 5/1982 | Inoue | 604/101 |
| 4,328,811 | 5/1982 | Fogarty | 604/99 |
| 4,479,497 | 10/1984 | Fogarty et al. | 604/103 |
| 4,526,175 | 7/1985 | Chin et al. | 604/98 |
| 4,606,347 | 8/1986 | Fogarty et al. | 604/102 |
| 4,637,396 | 1/1987 | Cook | 604/103 |
| 4,820,270 | 4/1989 | Hardcastle et al. | 604/96 |
| 4,946,440 | 8/1990 | Hall | 604/97 |
| 5,042,976 | 8/1991 | Ishitsu et al. | 604/100 |

Primary Examiner—John D. Yasko
Assistant Examiner—Mark Bockelman
Attorney, Agent, or Firm—Jones, Tullar & Cooper

[57] ABSTRACT

Disclosed herein is a double lumen catheter assembly having an expandable or inflatable balloon element which can be fully stretched longitudinally while preventing stretching of the catheter outer and inner tubes. The balloon element is fixedly attached at its respective ends to the open distal ends of the outer and inner tubes. An elongated flexible pusher member is adapted to be inserted into the inner catheter tube when the stretching of the balloon element is required. The pusher member has a hardness greater than the catheter tubes. When inserted into the inner catheter tube and moved relative to the outer catheter tube, the pusher member comes into abutting enagement with a rigid stop member provided in the distal end of the inner catheter tube. Continued forward movement of the pusher member relative to the outer catheter tube causes the balloon element to be stretched longitudinally into a geometric shape that provides for easy insertion into a blood vessel.

4 Claims, 1 Drawing Sheet

BALLOON CATHETER ASSEMBLY

This is a continuation of co-pending application Ser. No. 07/427,345 filed on Oct. 27, 1989.

BACKGROUND OF THE INVENTION

The present invention relates to an improved double lumen catheter wherein an expandable or inflatable balloon element can be longitudinally stretched into a reduced cross section to permit easy pre-inflation positioning within blood vessels.

Various catheter devices including a balloon catheter have been developed for dilating occluded blood vessels, for example. The balloon catheter includes a balloon element which, during positioning, is kept in a non-inflated condition to permit easy emplacement relative to an occlusion. When the balloon element is disposed immediately adjacent the occlusion being trated, it is expanded or inflated by introducing pressurized fluid into the balloon element to dilate the occlusion. It is preferable that the balloon element in its non-inflated condition have a small outer diameter so as to enable easy insertion or movement within blood vessels. However, there is the conflicting requirement that the balloon element have a large outer diameter so as to have an increased cross section when inflated, so that dilatation can be achieved more effectively and efficiently. Japanese Laid-Open Patent Application No. 53-125386 offers an effective solution to this problem by providing a double lumen catheter which comprises an elongated flexible outer tube, an elongated flexible inner tube disposed in and extending through the outer tube for relative movement to each other and a balloon element fixedly attached at its respective ends to the distal ends of the outer and inner tubes. In inserting the balloon catheter into a blood vessel, the outer and inner tubes are relatively displaced in opposite directions so as to stretch the balloon element longitudinally to have a reduced cross section.

However, the catheter of the aforementioned type has the disadvantage that due to the flexible nature of the outer and inner tubes which are generally made of an elastic material, it is not possible to stretch the balloon element sufficiently to obtain a reduced cross section as desired.

Accordingly, it is a primary object of the invention to provide an improved balloon catheter assembly wherein the balloon element can be stretched lengthwise to its full extent by preventing the stretching of the catheter tubes which would otherwise reduce the tension in the balloon.

SUMMARY OF THE INVENTION

The object stated above and other related objects of the invention are accomplished by providing a catheter assembly comprising a double lumen catheter including an elongated outer flexible tube and an elongated inner flexible tube movably disposed in the outer flexible tube, each of the outer and inner flexible tubes having an open distal end, the inner and outer tubes being longitudinally displaceable relative to each other; a balloon element fixedly attached at its respective ends to the open distal ends of the outer and inner tubes; stopper means provided in the distal end of the inner flexible tube; and an elongated pusher means movably disposed in the inner flexible tube and having a distal end operatively associated with the stopper means, the pusher means being adapted to be moved relative to the outer flexible tube for causing the balloon element to be stretched in the longitudinal direction to have a reduced cross section, whereby the balloon catheter is easily inserted into and moved within blood vessels.

The stopper means may be in the form of a rigid ring having a longitudinal section of smaller inside diameter which is adapted for abutting engagement by the distal end of the pusher means when stretching of the balloon element is required.

Preferably, a cord member having a resistance to stretching greater than that of the catheter tubes is disposed between the outer and inner catheter tubes and extends over a distance substantially equal to the length of the outer tube. The cord member is fixedly attached at its respective ends to the distal and proximal ends of the outer catheter tube to prevent the outer catheter tube from being stretched during the stretching of the balloon element.

Preferably, a rigid connector ring is provided adjacent the open distal end of the outer catheter tube. The open distal end of the outer tube is fitted over the connector ring for firm attachment thereto by fastener means. This arrangement serves to prevent the outer catheter tube from collapsing by the tightening pressure applied thereto. The proximal end of the balloon element is connected to a similar rigid connector ring in the same manner as described above.

BRIEF DESCRIPTION OF THE DRAWINGS

The invention will be better understood from the following detailed description of preferred embodiments of the invention, when taken in conjunction with the accompanying drawings, in which.

DETAILED DESCRIPTION OF PREFERRED EMBODIMENTS OF THE INVENTION

Figure 1:
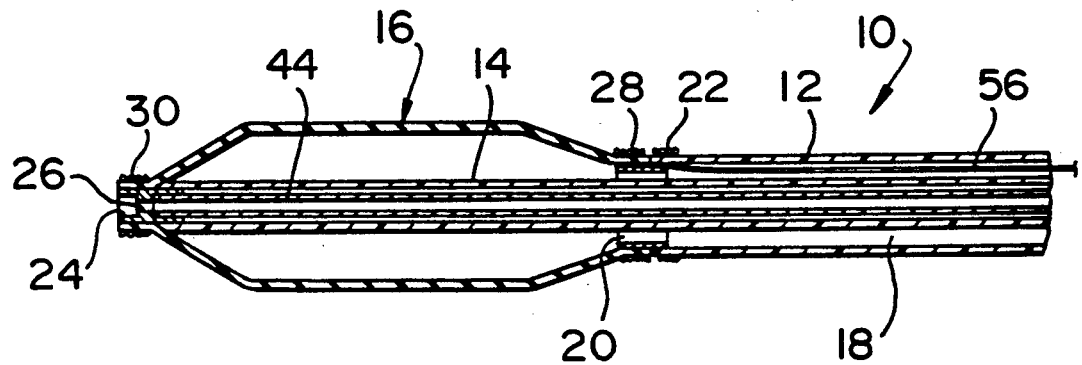
FIG. 1 is a sectional view of a distal end portion of a balloon catheter assembly in accordance with a first embodiment of the present invention, with a pusher member in abutting engagement with a stop ring attached to the distal end of the inner catheter tube.
Figure 2:
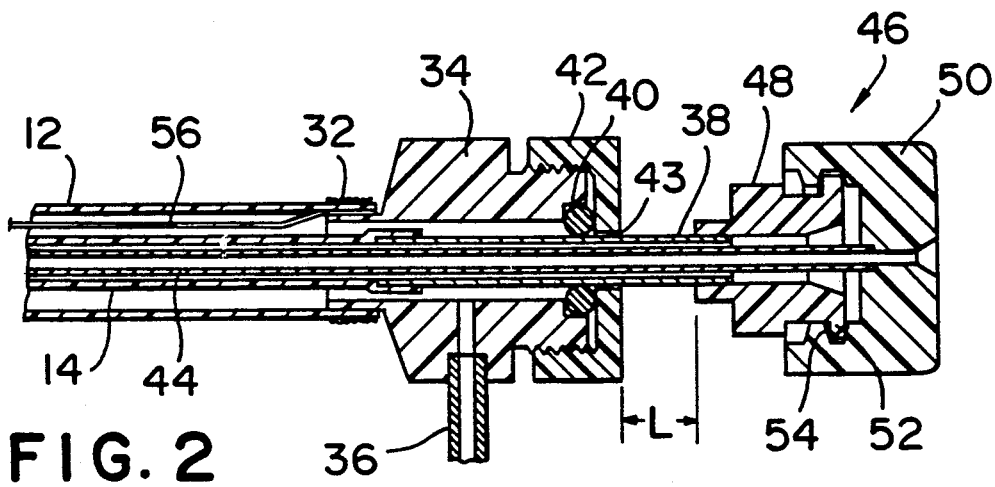
FIG. 2 is a sectional view of a proximal end portion of the balloon catheter assembly as shown in FIG. 1.

FIGS. 1 and 2 illustrate, respectively, a forward or distal end portion and a rearward or proximal end portion of a balloon catheter assembly of double lumen type 10 constructed in accordance with the teachings of the present invention. As shown, the catheter assembly 10 essentially consists of elongated outer and inner tubular members 12 and 14, and an expandable or inflatable balloon element 16. As is well known in the art, the catheter is utilized to dilate occluded blood vessels, take pressure measurements or make radiopaque fluid injections while the catheter remains within the vessel being trated. The outer tube 12, as well as the inner tube 14, of the catheter is often made of a flexible plastic material such as vinyl chloride, polyurethane, or the like. It is preferable to form the outer catheter tube 12 more flexible at its distal end portion than in the remaining portions so as to provide for ease of operation. The flexible nature of these tubes allows the double lumen catheter to conform to tortuous blood vessels. The inner catheter tube 14 is disposed within the outer catheter tube 12 in a generally coaxial relationship to define an annular space 18 therebetween. Any suitable fluid can be fed into the annular space 18 as desired. The inner catheter tube 14 is longitudinally displaceable relative to the outer tube 12 in a known manner.

With particular reference to FIG. 1, the open distal end of the catheter outer tube 12 is sealingly connected to a connector ring 20 using suitable fastener means 22 such as a fine thread which is tightly wound onto the outer tube distal end. It should be noted that the connector ring 20 is made of an inelastic material such as hard plastic or metal so as to prevent the open distal end of the outer catheter tube 12 from collapsing under the binding force applied from the fastener means thereto. Alternatively, the distal end portion of the outer tube may be bonded to the connector ring 20 by means of an adhesive material. Preferably, the cylindrical outer surface of the connector ring 20 may be rough so that it can firmly and frictionally engage the interior surface of the outer catheter tube 12 to prevent accidental slipping off of the outer tube 12 from the connection ring 20.

Another connector ring 24 is disposed in the open distal end of the inner catheter tube 14. As seen, it has a longitudinally extending section 26 of smaller inner diameter for the reason to be explained later. In the illustrated embodiment, the inner tube distal end is bonded to the ring 24 by means of an adhesive material. Alternatively, the connection of the inner tube 14 to the ring 24 may be achieved through use of suitable fastener means such as a fine thread in the same manner as described above. Since the ring 24 is hollow, a fluid such as physiologic saline, contrast injection or radiopaque material can be injected into the blood vessel through the inner catheter tube 14 and the ring 24, as the case may be. However, in place of the hollow connector ring, the open distal end of the inner catheter tube may be plugged with a solid connector piece (not shown). The balloon element 16 is fixedly and sealingly attached at its respective ends to the connector rings 20 and 24 to which the outer and inner catheter tubes 12, 14 are fixedly attached, by suitable fastener means 28 and 30, respectively.

Turning to FIG. 2, the open proximal end of the outer catheter tube 12 is fastened at 32, by suitable fastener means, to a conventional syringe fitting 34. The syringe fitting 34 has a fluid conduit 36 in fluid communication with the annular space 18 between the outer and inner catheter tubes 12 and 14 for injecting thereinto pressurized fluid from a fluid source (not shown) to expand or inflate the balloon element 16 for purposes of dilating the occlusion being treated. The syringe fitting 34 includes a cap 42 having a central opening 43 and adapted to be threadably received on a body portion of the fitting. The inner catheter tube 14 has a metallic slide tube 38 bonded to the proximal open end thereof. The slide tube 38 extends through the central opening 43 of the cap 42 in a sealing manner. A resilient O-ring 40 surrounding the slide tube 38 within the syringe fitting 34 provides such sealing effects. The internally threaded cap 42 engages an externally threaded portion of the fitting body portion for permitting a precise control of a contact pressure between the O-ring 40 and the slide tube 38 of the inner catheter tube 14.

The catheter assembly 10 also includes an elongated, flexible but generally inelastic pusher member 44 which is placed in the inner catheter tube 14 to cause the balloon element 16 to be stretched lengthwise in the manner to be described below. The pusher member 44 is utilized only when the longitudinal stretching of the balloon element 16 is required during inserting the catheter 10 into the blood vessel for emplacement of the balloon element 16 relative to occlusions or during removing the catheter from the vessel. To this end, the pusher member 44 is inserted into the inner catheter tube 16 and moved forward therealong until the leading end of the pusher member 44 comes into abutting engagement with the small inside diameter section 26 of the connector ring 24 to which the distal end of the inner catheter tube 14 is fixedly attached. As is understood, the smaller inside diameter section of the ring 24 serves as stop means for the pusher member 44. Thus, continued forward movement of the pusher member 44 relative to the outer catheter tube 12 will result in stretching of the balloon element 16 into a geometric shape that permits easy insertion into the blood vessel. The material from which the pusher member 44 is formed is selected to provide the member for sufficient strength to allow full stretching of the balloon element 16 against the reactive contractive force of the element. The pusher member 44 may be advantageously made of metal or other material having a hardness greater than the catheter tubular elements. In the illustrated embodiment, the pusher member 44 is in the form of a tube into which a guide wire (not shown) can be inserted. The guide wire is passed through the tubular pusher member and moved past the distal end portion of the inner catheter tube to guide the balloon element to an occlusion to be treated. A solid rod with a greater flexibility could be employed as pusher member.

The pusher member 44 can be operatively connected to the slide tube 38 and accordingly the inner catheter tube 14 by means of an interlocking mechanism 46 which comprises an operating knob 48 fixedly attached to the proximal end of the slide tube 38 and a handle member 50 fixedly attached to the proximal end of the pusher member 44, the operating knob 48 and the handle member 50 being adapted to be coupled to each other in a manner shown in FIG. 2. More specifically, the operating knob 48 has a circumferential projection 52 thereon which, in the interlocking position, is engagingly received in a complementary recess 54 formed in the handle member 50 to allow the inner catheter tube 14 and the pusher member 44 to be moved together to stretch the balloon element 16. Alternatively, the interlocking mechanism 46 may be arranged such that the handle member 50 may be threadably received onto the operating knob 48. In the interlocking position, there is a space L between the retainer cap 42 and the interlocking mechanism 46. As the pusher member 44 and the inner catheter tube 14 are moved together in the left-hand direction as viewed in FIGS. 1 and 2, a reduction the space L will result, indicating the extent to which the balloon element 16 has been longitudinally stretched.

According to another aspect of the present invention, a flexible but generally inelastic cord 56 is disposed within the annular space 18 between the outer and inner catheter tubes 12 and 14 and extends substantially over the entire length of the outer catheter 12. The respective ends of the cord 56 are tightly clamped between the outer catheter distal end and the connector ring 20 and between the outer catheter proximal end and the syringe fitting 34, respectively. In this manner, the cord 56 can function to avoid stretching of the outer catheter tube 12 which would otherwise prevent stretching of the balloon element 16 to the fullest extent. The cord 56 may be made of such a material as to give an excellent resistance to stretching. Suitable materials from which the cord 56 is formed include aramid, polyester, nylon, stainless steel fiber, carbon fiber or the like. The cord 56 enables the use of more flexible catheter tubes.

Figure 3:
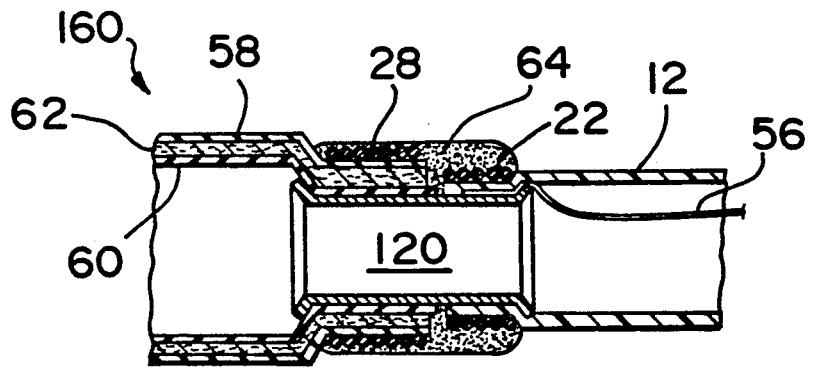
FIG. 3 is an enlarged fragmentary sectional view of a second embodiment of the invention, showing a modified connection ring disposed between the balloon element and the outer catheter tube.

FIG. 3 illustrates a modified connector ring 120 between the balloon element and the outer catheter tube 12. In that figure, like reference numerals are used to identify similar or corresponding parts of the first embodiment described above. The balloon element 16 has been replaced with a three-ply balloon element 160, and the inner catheter tube has been omitted for clarity. The balloon element 160 comprises outer and inner rubber plys 58, 60 and a fiber ply 62 disposed therebetween for purposes of preventing excessive expansion of the balloon element or withstanding excessively high fluid pressures so as to prevent rupture of the balloon element. In the embodiment shown in FIG. 3, fastener means 22 and 28 are embedded in an adhesive layer 64 applied over the fastener means. The adhesive layer 64 provides a smooth outer cylindrical surface which will allow the balloon catheter to be easily inserted into or withdrawn from the blood vessel. Advantageously, the connector ring 120 is flared outwardly at both ends thereof so that the balloon 160 and the outer catheter tube 12 are hardly slipped away from the connector ring 120. Again, the connector ring may preferably have a rough outer surface.

Numerous features and advantages of the present invention have been described in the foregoing, together with details of the structure and operation of the invention. The disclosure, however, is illustrative only, and changes may be made in detail without deviating from the spirit and scope of the invention.

What is claimed is:

1. A catheter assembly, comprising:
   a double lumen catheter including an elongated outer flexible tube and an elongated inner flexible tube movably disposed in the outer flexible tube, each of the outer and inner flexible tubes having an open distal end, the inner and outer tubes being longitudinally displaceable relative to each other;
   a balloon element fixedly attached at its respective ends to the open distal ends of the outer and inner tubes, and;
   an elastic connector ring disposed in the open distal end of the outer catheter tube, the open distal end of the outer tube and the proximal end of the balloon element being fitted over the connector ring for firm attachment thereto by fastener means, said connector ring being flared at both ends and being such that the open distal end of the outer catheter tube does not collapse under the force applied by the fastener means.

2. A catheter assembly as set forth in claim 1, further comprising a layer of adhesive material for providing a smooth outer surface, the fastener means being embedded in the layer of adhesive material.

3. A catheter assembly as set forth in claim 1, wherein the connector ring has a rough outer surface over which the open distal end of the outer catheter tube and the proximal end of the balloon element are fitted in frictionally engaging relationship.

4. A catheter assembly as set forth in claim 1, wherein the balloon element is comprised of outer and inner rubber plys and a fiber ply disposed therebetween for preventing lateral expansion of the balloon element or withstanding excessive fluid pressures so as to prevent rupture of the balloon element.

* * * * *